US006000395A

United States Patent [19]

Brown

[11] Patent Number: 6,000,395

[45] Date of Patent: Dec. 14, 1999

[54] AVALANCHE AND HYOTHERMIA PROTECTIVE SYSTEM

[76] Inventor: Norma Brown, 2721 Kings Hwy., apt. 4M, Brooklyn, N.Y. 11229

[21] Appl. No.: 09/074,130

[22] Filed: May 7, 1998

[51] Int. Cl.[6] .............................. A61N 16/00; H05B 6/00

[52] U.S. Cl. ................................ 128/202.19; 128/204.23; 128/205.23; 128/205.22; 128/202.15; 128/201.29; 219/211

[58] Field of Search ......................... 128/202.19, 202.15, 128/201.29, 201.28, 205.11, 205.26, 205.22, 205.23, 204.23, 206.21, 204.15, 204.16, 204.17, 201.21, 202.12, 203.26, 203.27

[56] References Cited

U.S. PATENT DOCUMENTS

| | | | |
|---|---|---|---|
| 3,227,208 | 1/1966 | Potter et al. | 128/201.21 |
| 3,496,703 | 2/1970 | Macleod et al. | 128/204.15 |
| 4,404,460 | 9/1983 | Kerr | 219/211 |
| 4,875,477 | 10/1989 | Waschke et al. | 128/206.21 |
| 4,998,296 | 3/1991 | Stames | 2/69.5 |
| 5,029,572 | 7/1991 | LeBlanc | 128/204.17 |
| 5,063,923 | 11/1991 | Peroni | 2/79 |
| 5,105,067 | 4/1992 | Brekkestran et al. | 219/497 |
| 5,400,934 | 3/1995 | Ducros | 128/202.15 |

FOREIGN PATENT DOCUMENTS

| | | | |
|---|---|---|---|
| 2375555 | 8/1978 | France | 2/69 |

*Primary Examiner*—John G. Weiss
*Assistant Examiner*—Teena Mitchell
*Attorney, Agent, or Firm*—Michael I. Kroll

[57] ABSTRACT

An avalanche and hypothermia protective system for detecting emergency situations and instances when a user is severely compromised by adverse atmospheric and climactic extremes, e.g. entombment by an avalanche or high altitude mountaineering, and providing relief for the detected emergency situation. The system includes a sensor housing to be worn on the head of the user including sensors for sensing certain conditions and generating a signal indicative of the conditions sensed. A backpack including a microprocessor therein is connected to the sensors for analyzing the generated signal to determine if an emergency situation exists. A device for relieving the emergency condition is connected to the microprocessor for providing relief to the user upon detection of an emergency condition and to provide support for preexisting conditions such as cold induced asthma. The sensors may sense at least one of skin temperature of the user, respiratory rate of the user, an amount of oxygen in the atmosphere surrounding the user, snow weight impacting on the user and noise level. The backpack may store an oxygen supply tank and a chemical heat pack for use in automatically relieving the detected emergencies. The system also includes a signal transmitter for transmitting a distress signal upon detection of an emergency condition or upon manual activation by the user. A supply of drinking fluids may also be stored within the backpack for providing liquid refreshment to the user when desired.

21 Claims, 9 Drawing Sheets

Fig. 3
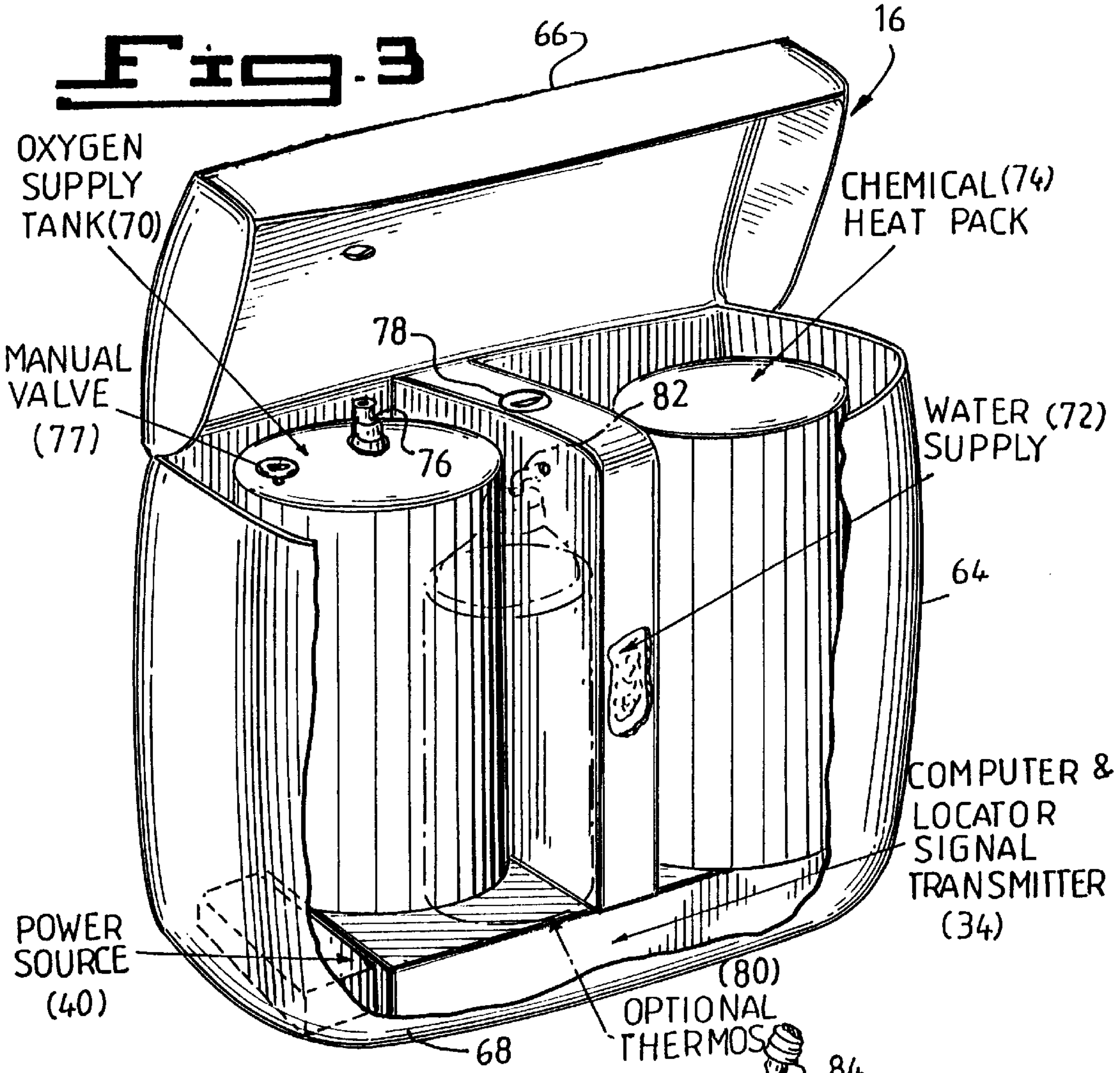
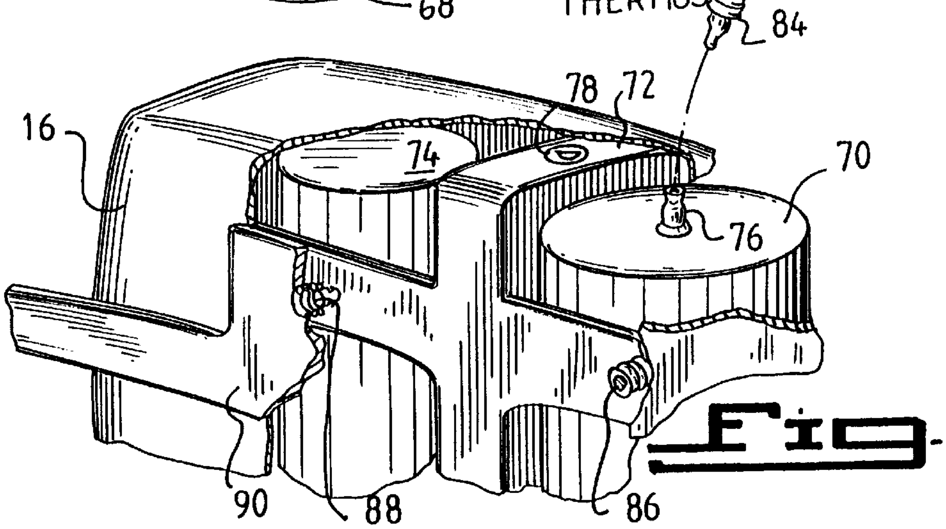
Fig. 3a

Fig. 4
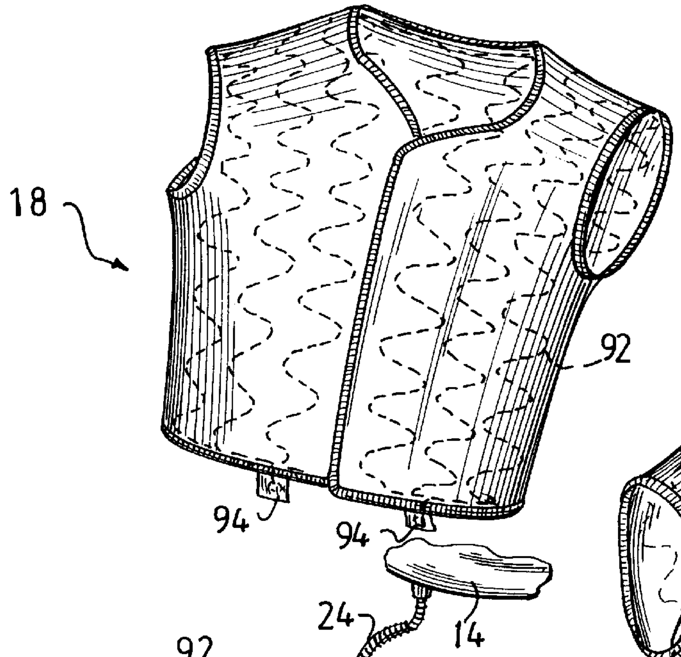
Fig. 5
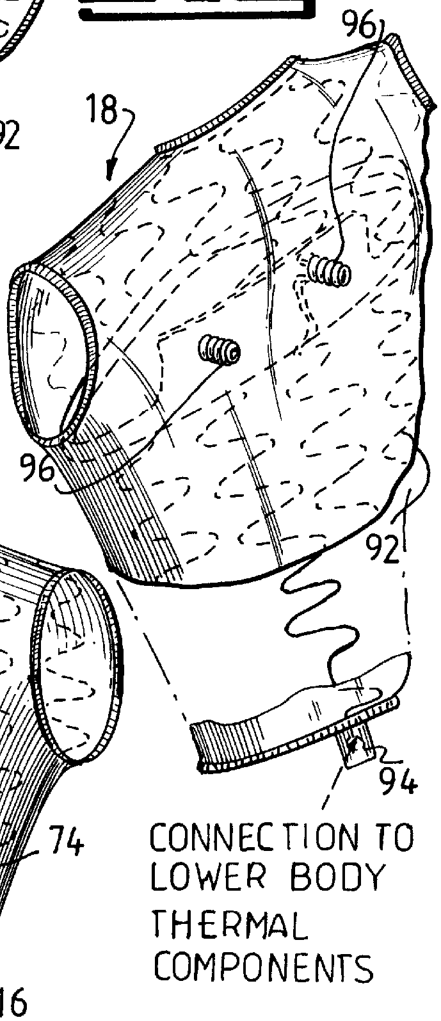
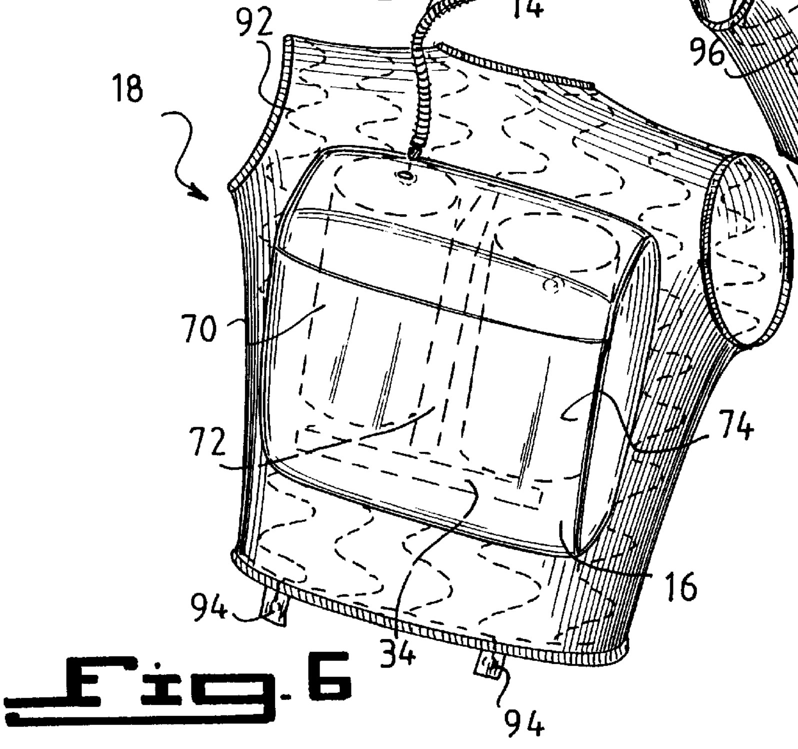
Fig. 6

AVALANCHE AND HYOTHERMIA PROTECTIVE SYSTEM

BACKGROUND OF THE INVENTION

1. Field of the Invention

The present invention relates generally to devices for protecting persons from emergency situations and, more specifically, to an avalanche and hypothermia protective system which is able to detect when an emergency situation exists and institute the proper protective measures upon determination of an emergency situation.

2. Description of the Prior Art

Numerous types of clothing for protecting persons from the elements have been provided in the prior art. For example, U.S. Pat. Nos. 3,911,913; 4,881,539; 5,027,807 and 5,109,215 all are illustrative of such prior art. While these units may be suitable for the particular purpose to which they address, they would not be as suitable for the purposes of the present invention as heretofore described.

U.S. Pat. No. 3,911,913

Inventor: Ethel L. June

Issued: Oct. 14, 1975

Compactly storable survival equipment that includes a protection suit and an inflatable collision cocoon. The double-walled cocoon entrance which can be closed by a suited means within the same, and the cocoon can then be inflated to its expanded and protective condition by the introduction of pressured gas into the double wall. A harness serves to secure the suited wearer in the cocoon, and survival devices are carried by the harness. The cocoon has flexibly covered openings whereby the suited wearer can alternatively withdraw his limbs into and extend them from the cocoon.

U.S. Pat. No. 4,881,539

Inventor: Adalbert Pasternack

Issued: Nov. 21, 1989

A protective suit has a supply of breathing air and includes a multiplicity of hollow chambers covering the body of the wearer which can be filled with breathing gas. The interiors of these chambers communicate with one another. The protective suit also includes hollow bodies which rest against the head, neck and upper torso region of a protective helmet portion. The interiors of these bodies communicate with those of the hollow chambers and with the interior of the protective helmet portion. The protective suit is configured for use for divers such that it is suitable not only for providing a sufficient volume for the supply of breathing gas and for thermal insulation but also, when it is filled, for first quickly pushing the diver up to the surface of the water and for providing a safe position of repose of the diver after ascent in which he can breathe freely, once he has reached the surface of the water. For this purpose, a source of breathing gas is connected to the hollow bodies and the connection between the hollow bodies and the hollow chambers is provided by a pretensioned transition element. In addition, the hollow chambers have an outlet which communicates with the interior of the protective helmet via a further pretensioned transition element. The opening pressure of the first mentioned transition element is less than the opening pressure of the second mentioned transition element.

U.S. Pat. No. 5,027,807

Inventor: Layton A. Wise et al.

Issued: Jul. 2, 1991

A protective garment or suit made of fluid impermeable material for use by workers in toxic and hostile environments having an air cooling device that divides air from a single airline supply into two separate fractions, one to provide respiratory air at the proper volume and pressure to a breathing mask and the other to provide cooling air at the proper volume and pressure to the inside of the suit to cool the body of the worker. The cooling device permits the delivery of different volumes of cooling air and respiratory air at the appropriate pressure. Further, the volumetric flow of respiratory air to the breathing mask can be adjusted by the worker while preventing it from being reduced below a predetermined safe minimum volumetric flow.

U.S. Pat. No. 5,109,215

Inventor: Everett Dennison

Issued: Apr. 28, 1992

A protective garment such as a surgeon's glove, is monitored for the occurrence of a breach in that garment. The monitoring is performed using an improved version of the system disclosed in U.S. Pat. No. 5,036,309, issued Jul. 30, 1991. The system is improved by adding monitors for ensuring that contacts are in proper and secure electrical contact with both the worker and the work piece. The system is further improved by adding electrical buses so that further contact monitors and garment integrity monitors can be added to the basic system and a start-up system integrity checking system. All monitors include current amplifying elements, such as transistors.

SUMMARY OF THE PRESENT INVENTION

The present invention relates generally to devices for protecting persons from emergency situations and, more specifically, to an avalanche and hypothermia protective system which is able to detect when an emergency situation exists and institute the proper protective measures upon determination of an emergency situation.

A primary object of the present invention is to provide an avalanche and hypothermia protective system that will overcome the shortcomings of prior art devices.

Another object of the present invention is to provide an avalanche and hypothermia protective system which is able to detect when a user encounters an emergency situation such as hypothermia or a severely impaired respiratory rate.

A further object of the present invention is to provide an avalanche and hypothermia protective system which is able to protect a user from being severely compromised by adverse atmospheric and climatic extremes.

A yet further object of the present invention is to provide an avalanche and hypothermia protective system which is able to provide basic physiological support for relieving acute or pre-existing conditions such as cold induced asthma.

A still further object of the present invention is to provide an avalanche and hypothermia protective system including a sensor device contained within a housing to be worn by a user for detecting emergency situations.

An additional object of the present invention is to provide an avalanche and hypothermia protective system wherein the sensor device contained within the sensor housing is able to monitor bodily and environmental conditions affecting the user.

A further object of the present invention is to provide an avalanche and hypothermia protective system which is able to provide a supply of oxygen to a user upon detection of a severely impaired respiratory rate.

Another object of the present invention is to provide an avalanche and hypothermia protective system including at least one of a vest, pants and socks connected to both the sensor device and supply tanks positioned within a backpack to be worn by the user to aid in providing relief upon determining the existence of an emergency condition. Alternatively, the avalanche and hypothermia protective system may be formed as a single piece body suit connected to both the sensor device and supply tanks.

An even further object of the present invention is to provide an avalanche and hypothermia protective system wherein a back pack is worn by the user for storing at least one of a supply of oxygen, a chemical heat pack containing a thermal fluid and a supply of water for use in relieving emergency situations.

A yet further object of the present invention is to provide an avalanche and hypothermia protective system which is able to provide a flow of heating fluid from the chemical heat pack through the vest, pants and socks or throughout the single piece body suit upon detection of a low body temperature.

A still further object of the present invention is to provide avalanche and hypothermia protective system which is able to transmit a distress signal upon either manual activation, detection by the sensor device of an emergency situation or detection of impact of a large amount of snow atop the user or a large noise consistent with that of an avalanche.

Another object of the present invention is to provide an avalanche and hypothermia protective system that is simple and easy to use.

A still further object of the present invention is to provide an avalanche and hypothermia protective system that is economical in cost to manufacture.

Additional objects of the present invention will appear as the description proceeds.

An avalanche and hypothermia protective system for detecting an emergency situation affecting a user of the system and providing relief for the detected emergency situation is described by the present invention. The avalanche and hypothermia protective system includes a sensor housing to be worn on the head of the user, the sensor housing includes at least one sensor therein for sensing a condition and generating a signal indicative of the sensed condition. A microprocessor is connected to the at least one sensor for analyzing the signal generated by the at least one sensor to determine if an emergency situation exists. A device for relieving the emergency condition is connected to the microprocessor for providing relief to the user upon determination that an emergency condition exists by the microprocessor. The at least one sensor may include a plurality of sensors which sense at least one of skin temperature of the user, respiratory rate of the user, snow weight impacting on the user, noise level and an amount of oxygen in the atmosphere surrounding the user. A backpack may be worn by the user for storing an oxygen supply tank and/or a chemical heat pack for use in automatically relieving the sensed emergencies. Additionally, a supply of drinking fluid may also be stored within the backpack for providing liquid refreshment to the user when desired.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

FIG. 1 is a perspective view of a skier using the avalanche and hypothermia protective system of the present invention;

FIG. 1*a* is a perspective view of a first embodiment of the sensor housing used with the avalanche and hypothermia protective system of the present invention showing an oxygen supply line in dashed lines;

FIG. 1*b* is a perspective partial cross-sectional view with parts cut away of the first embodiment of the sensor housing used with the avalanche and hypothermia protective system of the present invention for housing the plurality of sensors;

FIG. 1*c* is a side view of a second embodiment of the sensor housing used with the avalanche and hypothermia protective system of the present invention showing an oxygen supply line in dashed lines;

FIG. 1*d* is a front view of the second embodiment of the sensor housing used with the avalanche and hypothermia protective system of the present invention;

FIG. 1*e* is a perspective view of the second embodiment of the sensor housing used with the avalanche and hypothermia protective system of the present invention showing an oxygen supply line in dashed lines;

FIG. 1*f* is a front view of a third embodiment of the sensor housing used with the avalanche and hypothermia protective system of the present invention;

FIG. 1*g* is a back view of the third embodiment of the sensor housing used with the avalanche and hypothermia protective system of the present invention;

FIG. 1*h* is a front view of the third embodiment of the sensor housing used with the avalanche and hypothermia protective system of the present invention including an alternative face mask for supplying oxygen and liquid to the user;

FIG. 3 is a partial cross-sectional perspective view with parts cut away of the backpack of the avalanche and hypothermia protective system of the present invention;

Figure 7:
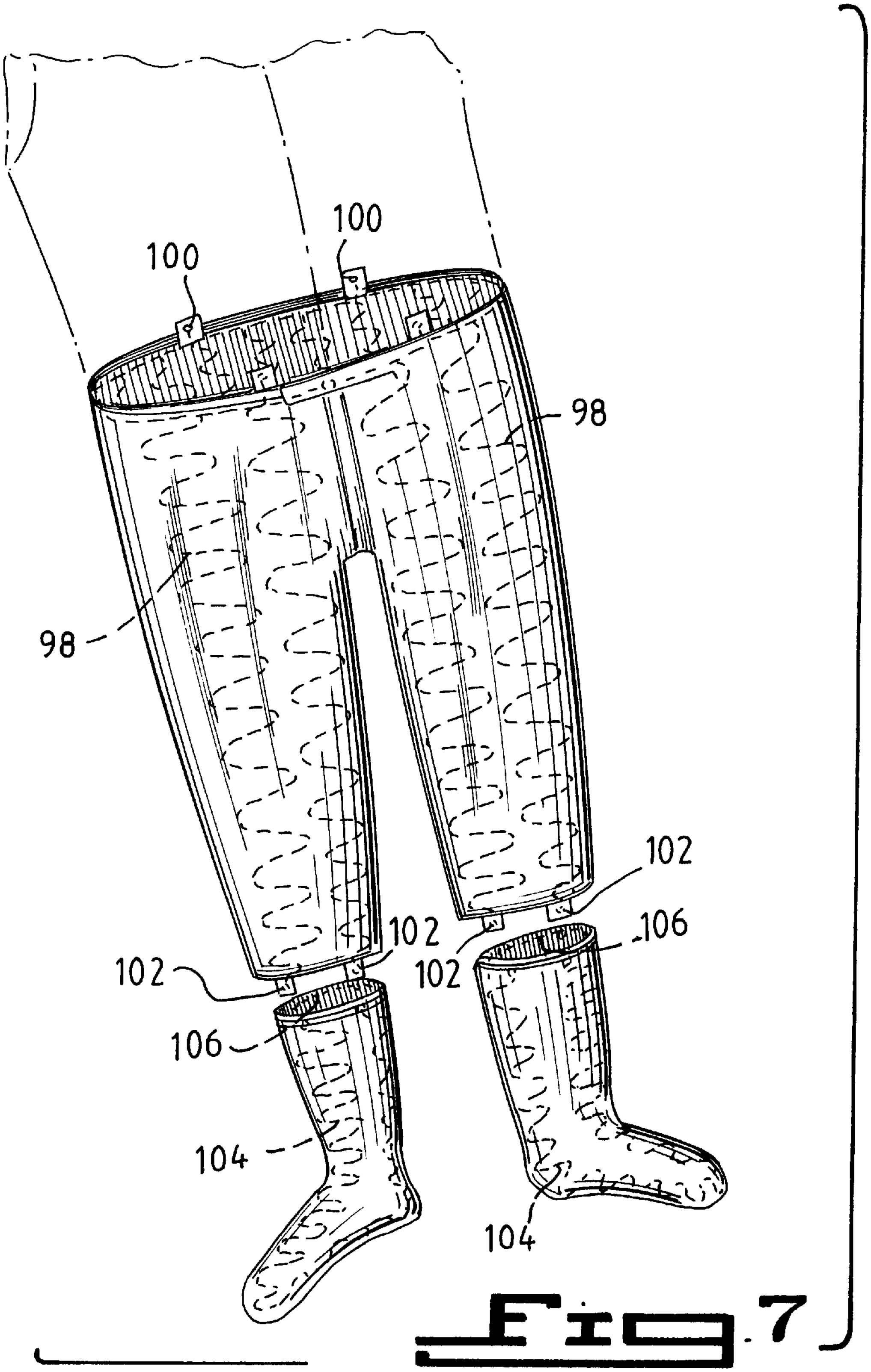
Figure 8:
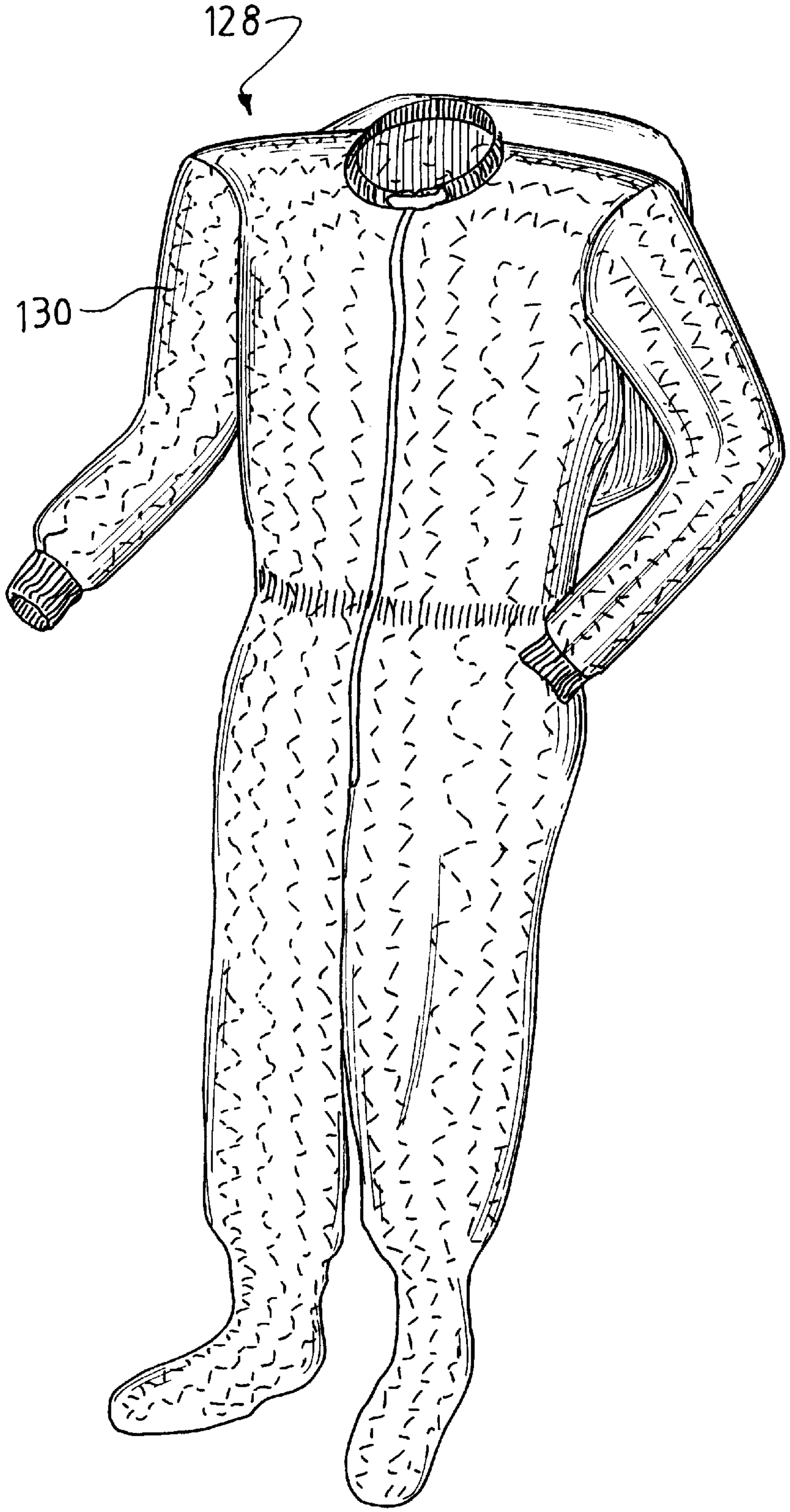

FIG. 3*a* is an exploded perspective view in partial cross-section illustrating a top portion of the back pack used with the avalanche and hypothermia protective system of the present invention;

FIG. 4 is a front perspective view of a vest used with the avalanche and hypothermia protective system of the present invention;

FIG. 5 is a back perspective view of the vest used with the avalanche and hypothermia protective system of the present invention having the backpack removed;

FIG. 6 is a back perspective view of a vest used with the avalanche and hypothermia protective system of the present invention including a back pack for retaining oxygen and heating fluids therein;

FIG. 7 is a perspective view of pants and socks used with the avalanche and hypothermia protective system of the present invention; and FIG. 8 is a perspective view of a single piece body suit used with the avalanche and hypothermia protective system of the present invention.

DESCRIPTION OF THE REFERENCED NUMERALS

Turning now descriptively to the drawings, in which similar reference characters denote similar elements throughout the several views, the Figures illustrate the avalanche and hypothermia protective system of the present invention. With regard to the reference numerals used, the following numbering is used throughout the various drawing figures.

10 avalanche and hypothermia protective system of the present invention
12 user of the avalanche and hypothermia protective system
14 first embodiment of sensor housing
16 backpack
17 waist and shoulder straps
18 vest
20 pants
21 socks
22 visor of first embodiment of sensor housing
24 oxygen line
26 mouth piece
28 nose piece
29 respiratory sensor probe
30 nose of user
31 tube for supplying liquid to the user's mouth
32 mouth of user
33 sensor probes
34 microprocessor
36 comparator
38 computer/processor
40 power source
42 sensor probes
43 tube for supplying heating fluid contained within the chemical heat pack to the vest, pants and socks
44 sensor for measuring skin temperature
46 a sensor for measuring respiration rate
48 sensor for measuring level or amount of oxygen in surrounding atmosphere
50 sensor for measuring snow weight
52 sensor for measuring noise
54 water sensor
60 oxygen supply
61 oxygen level in tank
62 locator/signal transmitter
64 housing of backpack
66 cover of backpack
68 base of housing
70 oxygen supply tank
72 water supply tank
74 chemical heat pack
76 valve on oxygen supply tank for connection to oxygen tube
77 manual activation valve on oxygen supply tank
78 cap on water supply tank
80 optional thermos
82 connection tube connection optional thermos to water supply tank
84 cap for sealing valve on oxygen supply tank
86 connector for connecting oxygen supply tank to oxygen tube
88 connector for connecting chemical heat pack to tubes in vest, pants and socks
90 rigid frame of backpack
92 heating fluid tubes extending through the vest
94 connection device within vest for connecting to heating fluid tubes extending through pants
96 connection device for connecting backpack to vest
98 heating fluid tubes extending through the pants
100 connection device within pants for connecting to heating fluid tubes extending through vest
102 connection device within pants for connecting to heating fluid tubes extending through socks
104 heating fluid tubes extending through the socks
106 connection device within socks for connecting to heating fluid tubes extending through pants
108 second embodiment of the sensor housing
110 face mask of second embodiment
112 collar section of second embodiment
114 head section of second embodiment
116 third embodiment of the sensor housing
118 first band of third embodiment
120 second band of third embodiment
122 third band of third embodiment
124 tube for supplying oxygen to nose of user
126 face mask of third embodiment
128 single piece garment
130 heating fluid tubes extending through single piece garment

DETAILED DESCRIPTION OF THE PREFERRED EMBODIMENT

Turning now descriptively to the drawings, in which similar reference characters denote similar elements throughout the several views, FIGS. 1 through 8 illustrate the avalanche and hypothermia protective system of the present invention indicated generally by the numeral 10.

Figure 1:

The avalanche and hypothermia protective system 10 continually monitors certain indicia relating to the physical and environmental conditions affecting a user 12 of the avalanche and hypothermia protective system 10. The avalanche and hypothermia protective system 10 as illustrated in FIG. 1 includes a sensor housing 14 connected to a backpack 16, a vest 18, pants 20 and socks 21. The avalanche and hypothermia protective system 10 is normally worn by the user 12 while performing strenuous activities and in treacherous conditions. The backpack 16 is worn by the user 12 via waist and shoulder straps 17 and the vest 18, pants 20 and socks 21 are worn similarly to conventional vests, pants and socks. Alternatively, the vest 18, pants 20 and socks 21 may be formed as a single piece outfit as will be described with specific reference to FIG. 8. This is shown in FIG. 1 in which the user 12 is skiing through rough terrain. These conditions present situations in which the user 12 may experience severely impaired respiratory patterns, develop hypothermia or even be caught in an avalanche. Such conditions are monitored by the avalanche and hypothermia protective system 10 and upon detection of a situation representative of an emergency, initiates measures to relieve the detected situation. Also seen in this figure are sensors 33 mounted on the sensor housing 14 for monitoring numerous bodily and environmental conditions surrounding the user 12.

Figure 1A:
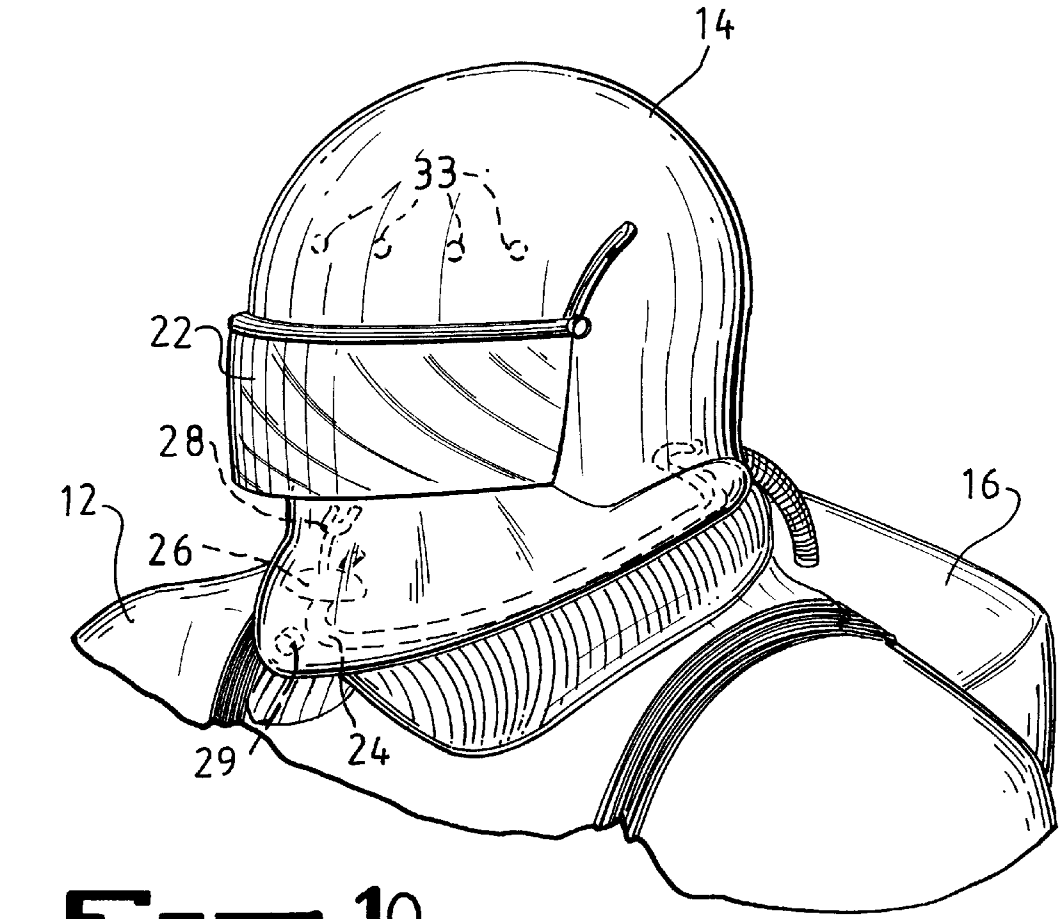
Figure 1B:
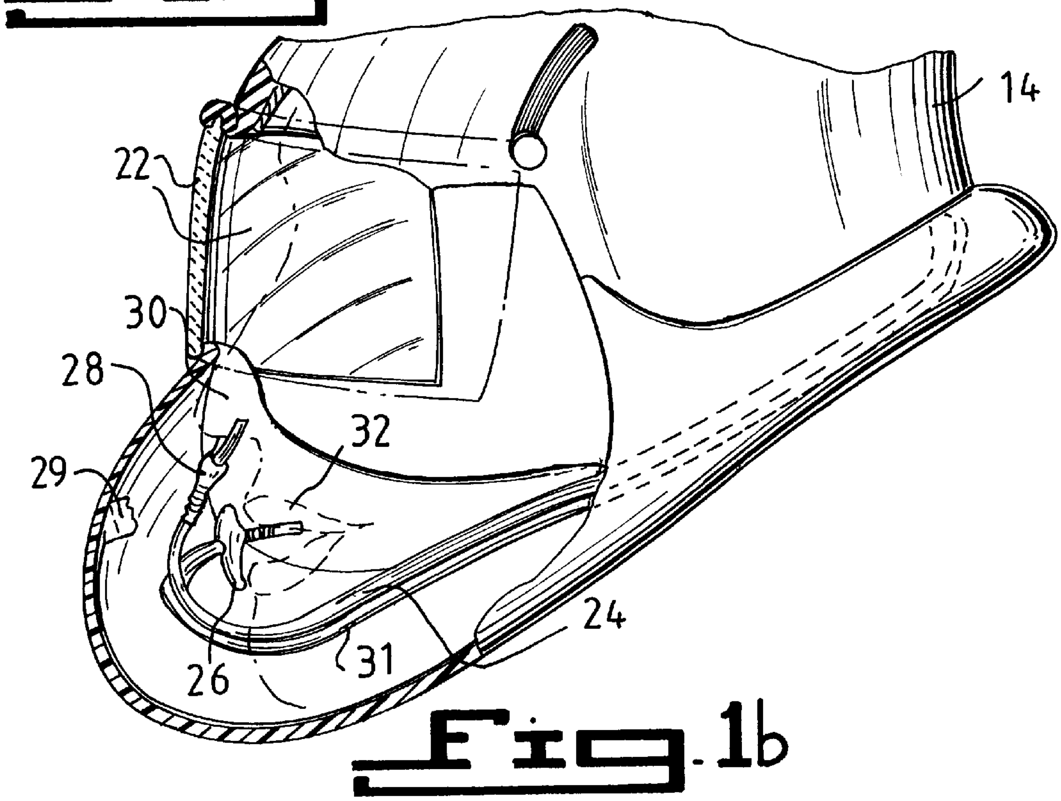

A first embodiment of the sensor housing 14 is illustrated in FIGS. 1*a* and 1*b*. The sensor housing 14 is in the form of a helmet to be worn on the user's head and includes a visor portion 22 through which the user 12 is able to see. The first embodiment of the sensor housing 14 also includes an oxygen line 24 having a mouth piece 26 and nose piece 28. The mouth piece 26 is positioned to deliver oxygen and liquid refreshment to the user's mouth and the nose piece 28 is positioned to deliver oxygen to the user's nose through the oxygen line 24.

The oxygen line 24 extends between the user's mouth and nose and the backpack 16. The oxygen line 24 is connected to an oxygen tank positioned within the backpack 16 for receiving the supply of oxygen. The oxygen line 24 extends through the sensor housing 14 and is securely attached to and within the sensor housing 14 thus preventing the oxygen line 24 from being either torn or pulled from its position during an avalanche or other turbulence inducing situation.

Also positioned within the sensor housing 14 is a respiratory sensor probe 29. The respiratory sensor probe 29 is positioned to measure the respiratory rate of the user 12. Upon detection of an irregular or severely impaired respiratory rate by the respiratory sensor probe 29, the oxygen tank will be controlled to automatically supply oxygen through the oxygen line 24 to the user. The oxygen tank 24 also includes a control valve for manually controlling the flow of oxygen through the oxygen line 24 as will be discussed hereinafter with specific reference to FIGS. 3 and 3*a*. As is illustrated in FIG. 1*b*, a tube 31 is connected to a supply of water or liquid within the backpack 16 for delivering liquid from the supply tank to the user's mouth 32. The oxygen line 24 and tube 31 both extend through the sensor housing 14 and are securely attached to and within the sensor housing 14 thus preventing the oxygen line 24 and tube 31 from being either torn or pulled from their position during an avalanche or other turbulence inducing situation. The respiratory sensor probe 29 is also illustrated in position for measuring the respiratory rate of the user 12.

Figure 1C:
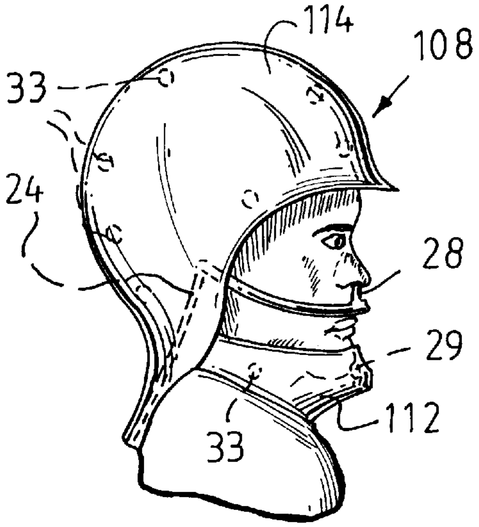
Figure 1D:
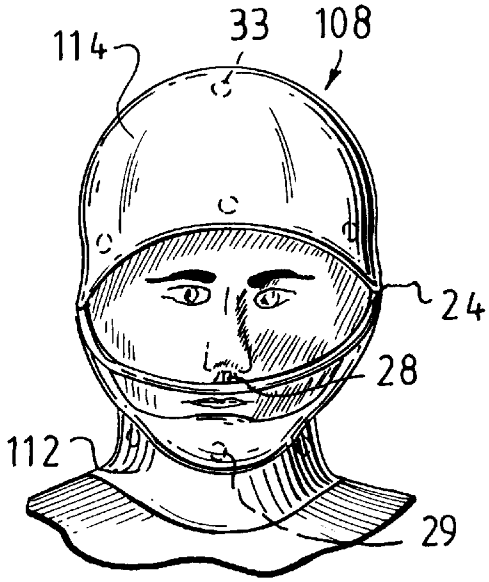
Figure 1E:
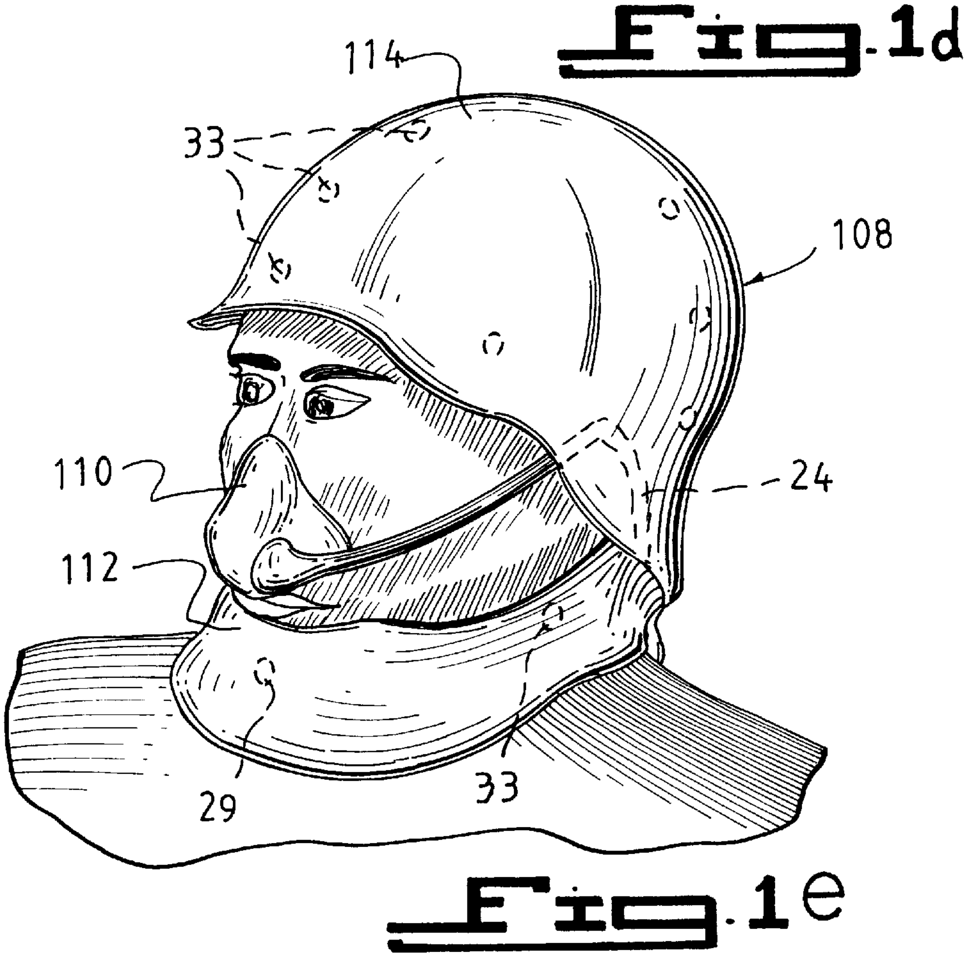

A second alternate embodiment of the sensor housing 108 is illustrated in FIGS. 1*c*, 1*d* and 1*e*. The second embodiment of the sensor housing 108 is also in the form of a helmet. However, this embodiment does not include the visor portion 22. The helmet 108 does include the oxygen line 24 having the nose piece 28 positioned to deliver oxygen to the user's nose 30. The oxygen line 24 is connected to the oxygen tank positioned within the backpack 16 for receiving the supply of oxygen and extends between the user's nose 30 and the backpack 16. Alternatively, the helmet 108 may include a face mask 110 for covering both the nose and mouth of the user 12 and supplying oxygen thereto through the oxygen line 24. The helmet 108 includes a collar portion 112 extending around the neck and possibly covering the chin of the user 12. Certain sensor probes such as for measuring the respiratory rate 29 and possibly the pulse or skin temperature of the user are positioned in the collar portion 112. The remaining sensor probes 33 are positioned throughout a head covering portion 114 of the helmet 108.

Figure 1F:
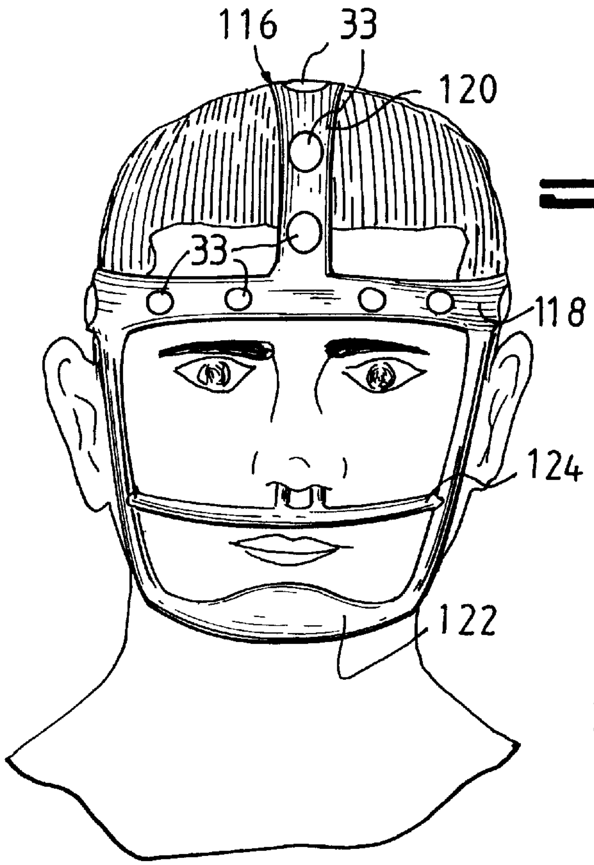
Figure 1G:
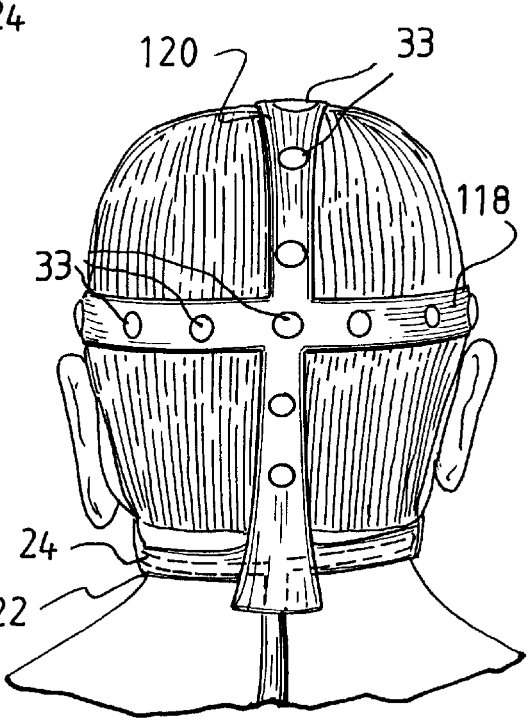
Figure 1H:
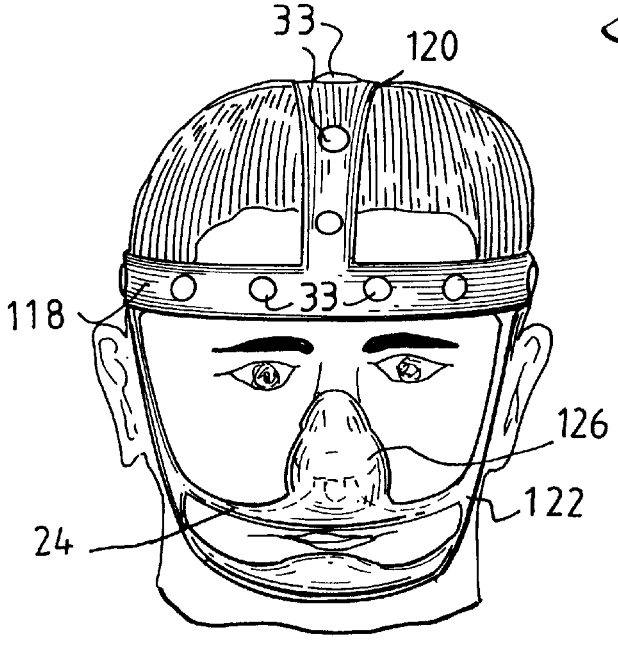
Figure 2:
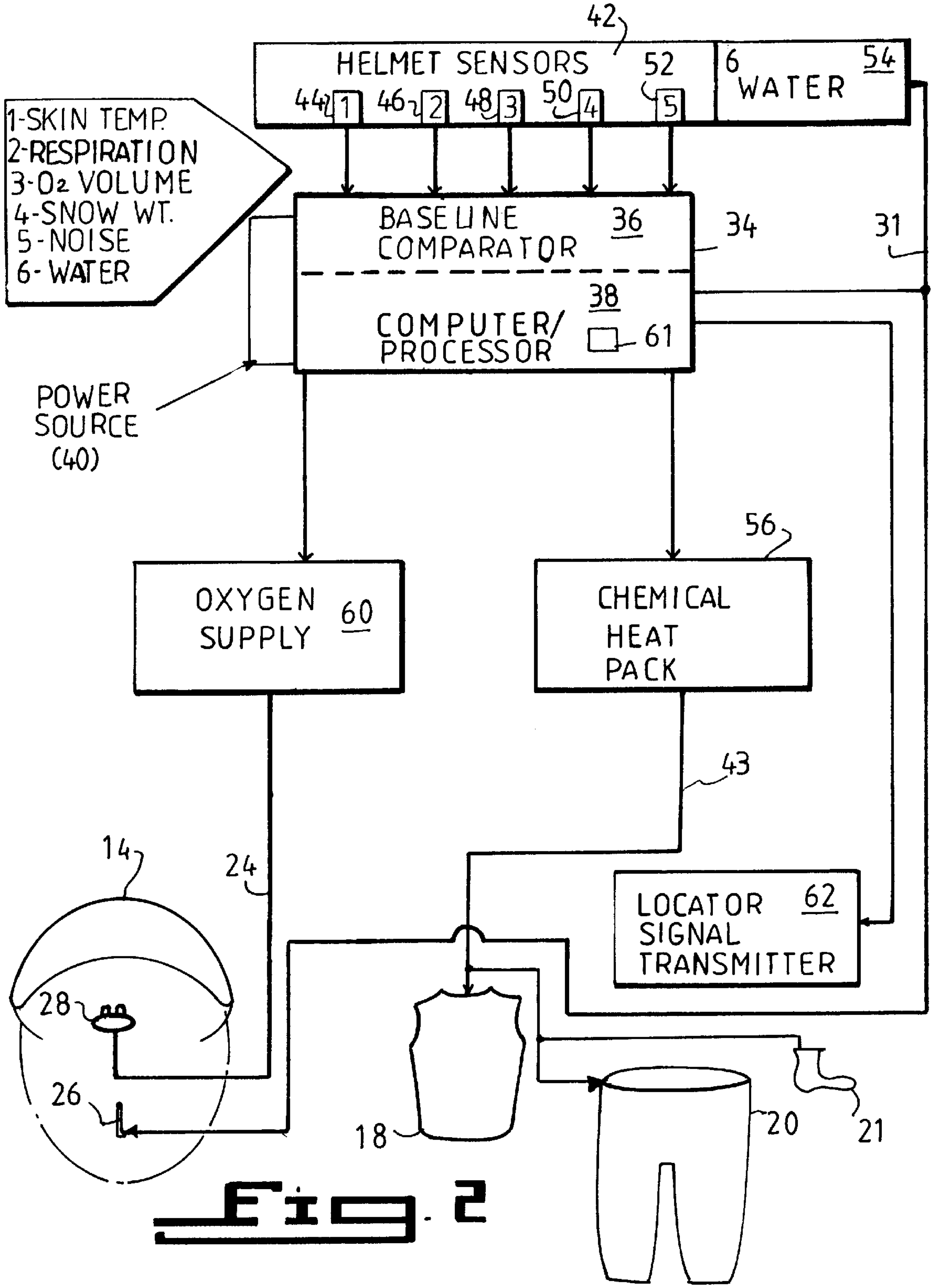
FIG. 2 is a block diagram of the avalanche and hypothermia protective system of the present invention.

A third embodiment for the sensor housing 116 is illustrated in FIG. 1*f*, 1*g* and 1*h*. This embodiment is formed from a first band 118 extending around the user's head, a second band 120 extending from a central point on the first band 118 over the user's head and down the back of the user's head to the neck and a third band 122 extending from the first band 118 around the user's chin. The plurality of sensor probes 33 for sensing the different bodily functions and atmospheric conditions are positioned along the lengths of the first and second bands 118 and 120, respectively. A tube 124 extending from the oxygen line 24 supplies oxygen to the nose of the user as illustrated in FIG. 1*f*. Alternatively, a face mask 126 can extend from the oxygen line 24 to supply oxygen to the nose and mouth of the user as illustrated in FIG. 1*h*.

The plurality of sensor probes 33 for sensing particular bodily and environmental conditions affecting the user 12 are strategically positioned throughout the sensor housing worn by the user 12. The sensor probes 33 generate signals indicative of the sensed values and are connected to deliver the generated signals to a microprocessor 34 as illustrated in block diagram form in FIG. 2. The microprocessor 34 may be positioned in either the sensor housing or within the backpack 16 and includes a comparator 36 and a computer/processor 38. A power source 40 is connected to supply power to the microprocessor 34. The microprocessor 34 is connected to the sensor probes 42, e.g. the respiratory sensor probe 29 and the sensor probes 33, positioned within the sensor housing. The sensor probes 42 include but are not limited to a sensor for measuring skin temperature 44, a sensor for measuring respiration rate 46, a sensor for measuring an amount of oxygen in the surrounding atmosphere 48, a sensor for measuring snow weight 50, a sensor for measuring noise 52 and a water sensor/tank 54.

The sensor for measuring skin temperature 44 includes a probe positioned either within the helmet 14 or on the body of the user 12 and measures the skin temperature of the user 12. The sensor for measuring skin temperature 44 generates a signal indicative of the measured value which is transmitted to the comparator 36 in the microprocessor 34. The comparator 36 compares the received signal to a reference value to determine if the user's 12 body temperature is below a predefined body temperature. The computer/processor 38 of the microprocessor 34 is connected to a chemical heat pack 56 also stored within the backpack 16. The chemical heat pack 56 is connected to tubes extending through the vest 18, pants 20 and socks 21 as will be described in further detail hereinafter. The chemical heat pack 56 supplies a heating fluid contained therein through a tube 43 to the vest 18, pants 20 and socks 21 when it is determined that the user's 12 body temperature is below the predefined body temperature.

The sensor for measuring respiration 46 includes a probe positioned in the sensor housing at a position adjacent the mouth and nose of the user. The sensor for measuring respiration 46 measures the respiration rate of the user 12 and generates a signal indicative of the measured value which is transmitted to the comparator 36 in the microprocessor 34. The comparator 36 compares the received signal to a reference value to determine if the user's 12 respiration rate is below a predefined rate. The computer/processor 38 of the microprocessor 34 is connected to an oxygen supply tank 60 stored within the backpack 16. The oxygen supply tank 60 is connected to the oxygen tube 24 extending through the helmet 14 for controlling the supply of oxygen through the oxygen tube 24 based upon the measurement of the user's 12 respiration rate.

The sensor for measuring an amount or level of oxygen in the surrounding atmosphere 48 includes a probe positioned on the sensor housing for measuring the amount of oxygen within the surrounding atmosphere. This is useful to determine when the level of oxygen surrounding the user is low making it difficult to breathe. The sensor for measuring oxygen level in the surrounding atmosphere 48 generates a signal indicative of the measured value which is transmitted to the comparator 36 in the microprocessor 34. The comparator 36 compares the received signal to a reference value to determine if the oxygen level of the surrounding atmosphere is below a predefined critical value. The computer/processor 38 of the microprocessor 34 will then automatically cause oxygen to be supplied through the oxygen tube 24 to aid the breathing of the user. The oxygen tank also includes a meter thereon for displaying an amount of oxygen in the tank as will be discussed with specific reference to FIG. 2.

The sensor for measuring snow weight 50 includes a probe positioned on the sensor housing and measures the weight of snow atop the sensor housing. This is useful in determining if the user 12 has been covered by snow during an avalanche. The sensor for measuring snow weight 50 generates a signal indicative of the measured value which is transmitted to the comparator 36 in the microprocessor 34. The comparator 36 compares the received signal to a reference value to determine if the snow weight is above or equal to a predefined weight consistent with being covered by snow in an avalanche. The computer/processor 38 of the microprocessor 34 is connected to a locator/signal transmitter 62 for transmitting a distress signal when it is determined that the user has been covered by snow in an avalanche.

The sensor for measuring noise 52 includes a probe positioned on the sensor housing which measures the noise level in the surrounding atmosphere. This is useful in determining when an avalanche is occurring as a large noise is associated with the snow falling during the avalanche. The sensor for measuring noise 52 generates a signal indicative of the measured noise level. The generated signal is transmitted to the comparator 36 in the microprocessor 34. The comparator 36 compares the received signal to a reference value indicative of a noise level consistent with an avalanche, whereby upon determining the noise level is above the reference level a determination that an avalanche has occurred is made. The computer/processor 38 of the microprocessor 34 is connected to a locator/signal transmitter 62 for transmitting a distress signal when it is determined that the noise level is above the predefined level and thus indicative of an avalanche.

The locator/signal transmitter 62 is also equipped with a manual switch which the user can activate to send a distress signal when lost or in a troubling situation not sensed by the sensors of the system. Furthermore, the microprocessor 34 will activate the locator/signal transmitter 62 to transmit a distress signal upon sensing of an emergency situation by any of the other sensors.

Also positioned within the back pack 16 and connected through the tube 31 to the mouthpiece 26 is a supply of a drinking liquid 54, e.g. water or a hot liquid such as hot chocolate or coffee. The drinking liquid is supplied through the tube 31 upon determining the user is in need of a drink either based upon the conditions sensed by the other sensors or via a manual control activated by the user 12.

FIG. 3 illustrates a preferred embodiment of the backpack 16. This embodiment shows the backpack 16 including a housing 64 having a pivoting top 66 for providing access to the inside of the backpack 16. Positioned at a base 68 of the housing 64 are the microprocessor 34 including the comparator, computer/processor and the signal transmitter 62. Also positioned adjacent the microprocessor 34 is the power source 40. Located above the microprocessor 34 are an oxygen supply tank 70, a water supply tank 72 and a chemical heat pack 74. The oxygen supply tank 70, water supply tank 72 and chemical heat pack 74 are all thermally insulated from one another and thereby prevent the heat from the chemical heat pack 74 from effecting the temperature of the water supply 72 and oxygen supply tank 70 or vice versa. The oxygen supply tank 70 includes a valve 76 for filling the tank 70 with oxygen. A manual activation valve 77 is also positioned on the oxygen supply tank 70 for manually controlling a supply of oxygen to the user through the oxygen tube 24. The oxygen supply tank 70 may also include a meter positioned thereon for displaying an amount of oxygen in the tank 70. The water supply tank 72 includes a removable cap 78 for use in filling the tank 72 with a desired liquid and for connection to the tube 31 for delivering the liquid within the tank 72 to the user 12. The chemical heat pack 74 is connected to the vest 18, pants 20 and socks 21 for supplying the heating liquid through the tubes extending therethrough. The backpack 16 also provides room for an optional thermos 80 for storing additional heated drinking liquids. The optional thermos 76 is connected to the water supply tank 72 via a connection tube 82 which provides the tank 72 with an additional supply of liquid once the tank 72 is emptied.

An enlarged view of the top side of the backpack 16 is illustrated in FIG. 3*a*. As can be seen from this figure, the valve 76 includes a removable cap 84 for sealing the valve 76 closed after filling the tank 70 with oxygen. The oxygen supply tank 70 further includes a connector 86 for connecting the oxygen supply tank 70 to the oxygen tube 24 in order to deliver the oxygen to the user 12 and a manually controlled activation valve 77 for manually controlling the supply of oxygen through the tube 24. The chemical heat pack 74 also further includes a connector 88 for connecting the chemical heat pack 74 to the tubes extending through the vest 18, pants 20 and socks 21 or through the one piece garment for providing the heating fluid thereto and warming the user. The backpack 16 is supported by a rigid frame 90 which provides support to the backpack 16 and allows for the oxygen supply tank 70, the water supply tank 72 and the chemical heat pack 74 to be carried therein. The backpack 16 is fully padded to prevent rupturing of the oxygen supply tank 70, the water supply tank 72 and the chemical heat pack 74 and also prevent injury to the user should the user fall down atop the backpack 16. Furthermore, the backpack 16 is made of a waterproof material which prevents any water form being absorbed thereby and entering the inside of the backpack 16.

FIG. 4 illustrates a front view of the vest 18 for use with the avalanche and hypothermia protective system 10. The vest 18 includes a plurality of tubes 92 extending therethrough. The tubes 92 provide a path for the heating fluid to flow throughout the vest 18 and thereby warm the upper body of the user 12. Alternatively, the tubes 92 may be replaced by conductive coils which run through the area of the vest 18. In this instance, the chemical heat supply 74 would consist of a voltage source. Upon activation of the heat pack 74, a voltage is caused to flow through the conductive coils causing them to heat up and warm the upper body of the user 12. The vest 18 is worn by the user 12 as would a conventional vest and may be worn either over or under other layers of clothing. The vest 18 also includes a device 94 for connecting the thermal components, either the heating tubes 92 or the conductive coils, to the lower body thermal components such as the pants 20.

FIG. 5 illustrates a back view of the vest 18 for use with the avalanche and hypothermia protective system 10. From this view it can be seen that the vest 18 includes at least one device 96 for connection of the backpack thereto. This device connects to the rigid frame 90 of the backpack 16 securing it to the vest 18. The backpack 16 is illustrated as being connected to the vest 18 in FIG. 6. This figure illustrates the components within the backpack 16 in dashed lines and also shows the connection of the oxygen supply tank 70 to the oxygen tube 24. As can be seen from this figure, the oxygen tube 24 leads to the sensor housing through which it extends to supply oxygen from the oxygen supply tank 70 to the mouth and nose area of the user 12.

The pants 20 and socks 21 for use with the avalanche and hypothermia protective system 10 are illustrated in FIG. 7. The pair of pants 20 includes a plurality of tubes 98 extending therethrough. The tubes 98 provide a path for the heating fluid to flow throughout the pair of pants 20 and thereby warm the lower body of the user. Alternatively, the tubes 98 may be replaced by conductive coils which run through the area of the pair of pants 20. In this instance, the chemical heat supply 74 would consist of a voltage source. Upon activation of the heat pack 74, a voltage is caused to flow through the conductive coils causing them to heat up and warm the lower body of the user 12. The pair of pants 20 is worn by the user as would a conventional pair of pants and may be worn either over or under other layers of clothing. The pair of pants 20 includes a device 100 for connecting the thermal components, either the heating tubes 98 or the conductive coils, to the device 94 of the vest 18. The pair of pants 20 also includes a device 102 for connecting the thermal components, either the heating tubes 98 or the conductive coils, to the thermal components of the socks 21.

The pair of socks 21 includes a plurality of tubes 104 extending therethrough. The tubes 104 provide a path for the heating fluid to flow throughout the pair of socks 21 and thereby warm the feet of the user. Alternatively, the tubes 104 may be replaced by conductive coils which run through the area of the pair of socks 21. In this instance, the chemical heat supply 74 would consist of a voltage source. Upon activation of the heat pack 74, a voltage is caused to flow through the conductive coils causing them to heat up and warm the feet of the user 12. The pair of socks 21 is worn by the user as would a conventional pair of socks and may be worn either over or under other layers of clothing. The pair of socks 21 includes a device 106 for connecting the thermal components, either the heating tubes 104 or the conductive coils, to the device 102 of the pair of pants 20.

FIG. 8 illustrates an alternate one piece garment 128 which may be worn by the user in place of the vest 18, pants 20 and socks 21 combination. The one piece garment 128 includes a plurality of tubes 130 extending therethrough. The tubes 130 provide a path for the heating fluid to flow throughout the garment 128 and thereby warm the entire body of the user 12. Alternatively, the tubes 130 may be replaced by conductive coils which run through the area of the garment 128. In this instance, the chemical heat supply 74 would consist of a voltage source. Upon activation of the heat pack 74, a voltage is caused to flow through the conductive coils causing them to heat up and warm the entire body of the user 12. The one piece garment 128 is worn by the user as would a conventional one piece garment and may be worn either over or under other layers of clothing. Furthermore, the one piece garment 128 will include a device for attaching the backpack 16 thereto on a back side thereof The operation of the avalanche and hypothermia protective system 10 will now be described with reference to the figures and specifically FIG. 2. In operation, the avalanche and hypothermia protective system 10 is to be worn by the user 12. The user 12 will first make sure that the oxygen supply tank 70, the water supply tank 72 and the chemical heat pack 74 are filled with the appropriate substance. If an optional thermos 80 is used, it is filled and connected to the water supply tank 72. The user 12 will then connect the sensor housing to the backpack 16 such that the oxygen tube 24 is connected to the oxygen supply tank 70, the tube 31 is connected to the water supply tank 72 and the plurality of sensors 42 are connected to the microprocessor 34. The backpack 16 can now be secured to the vest 18 or back of the one piece garment 128 by connecting the connection device 96 to the rigid frame of the backpack 16.

Once the backpack 16 is secured to the vest 18 or the one piece garment 128, the vest 18, pants 20 and socks 21 or one piece garment 128 are now placed on by the user 12 and worn as would any conventional piece of clothing of a similar type. If the vest 18, pants 20 and socks 21 combination is being worn by the user, the device 94 is now connected to the device 100 for connecting the thermal components, either the heating tubes 92 or the conductive coils, of the vest 18 to the thermal components, either the heating tubes 98 or the conductive coils, of the pair of pants 20. The device 102 is now connected to the device 106 for connecting the thermal components, either the heating tubes 98 or the conductive coils, of the pair of pants 20 to the thermal components, either the heating tubes 104 or the conductive coils, of the pair of socks 21. The user 12 is now wearing the avalanche and hypothermia protective system 10 of the present invention and upon activation of the system is ready to brave the elements.

When the user 12 turns the system on, the sensors begin to monitor their respective conditions. The skin temperature sensor 44 will continually measure the skin temperature of the user and generate signals indicative of the measured skin temperature. The sensed values will continually be transmitted to the microprocessor 34 in which the signals are compared to a reference value. Based upon the comparison a determination will be made as to whether the user is suffering from hypothermia. If it is determined that the user 12 is suffering from hypothermia, the chemical heat pack 74 will be activated to allow the heating fluid to flow through the tubes in the vest 18, pants 20 and socks 21 to warm the user and raise the body temperature.

The respiration sensor 46 will continually measure the respiration rate of the user and generate signals indicative of the measured respiration rate. The sensed values will continually be transmitted to the microprocessor 34 in which the signals are compared to a reference value. Based upon the comparison a determination will be made as to whether the user is suffering from a respiratory ailment. If it is determined that the user 12 is suffering from a respiratory ailment, the oxygen supply tank 70 will be activated to allow oxygen to flow through the tube 24 and provide oxygen to the nose and mouth of the user.

The oxygen level sensor 48 will continually measure the level or amount of oxygen in the atmosphere surrounding the user to determine if the level of oxygen in the surrounding atmosphere is below a predetermined critical level and generate signals indicative of the measured oxygen level of the atmosphere. The sensed values will continually be transmitted to the microprocessor 34 in which the signals are compared to a reference value. Based upon the comparison a determination will be made as to whether the oxygen level in the surrounding atmosphere is low. If it is determined that the oxygen level in the surrounding atmosphere is low, the oxygen tank will be automatically controlled to supply a flow of oxygen through the oxygen tube 24 to the user's mouth and nose to aid the user in breathing.

The snow weight sensor 50 will continually measure the snow weight impounding the user to determine if the user has been covered by snow in an avalanche and generate signals indicative of the measured snow weight. The sensed values will continually be transmitted to the microprocessor 34 in which the signals are compared to a reference value. Based upon the comparison a determination will be made as to whether the user has been covered by snow in an avalanche. If it is determined that the user 12 has been covered by snow in an avalanche, the signal transmitter 62 is activated to transmit a distress signal indicating the location of the user.

The noise sensor 52 will continually measure the noise in the area surrounding the user to determine if the user has been in an area in which avalanche has occurred and generate signals indicative of the measured noise level. The sensed values will continually be transmitted to the microprocessor 34 in which the signals are compared to a reference value. Based upon the comparison a determination will be made as to whether the user has been in an area in which avalanche has occurred. If it is determined that the user 12 has been in an area in which avalanche has occurred, the signal transmitter 62 is activated to transmit a distress signal indicating the location of the user.

The water supply tank 72 may be manually activated by the user to supply a drink through the tube 31 and to the user for drinking when desired. The water supply tank 72 may also be automatically activated to supply a drink to the user upon a detection of any or all of the above described emergencies.

The present invention is not meant to be limited to sensing only or any combination of the above describe emergencies in the above described ways. In practice, the present invention can sense for any desired condition and use any applicable measures for relieving the sensed emergency in a manner consistent with the present invention. For example, the back pack is not limited to retaining solely an oxygen supply tank, water tank and chemical heat pack but may house anything desired for providing relief for a desired sensed emergency which can adequately be stored therein.

From the above description it can be seen that the avalanche and hypothermia protective gear of the present invention is able to overcome the shortcomings of prior art devices by providing avalanche and hypothermia protective gear which is able to detect when a user encounters an emergency situation such as hypothermia or irregular respiratory rate. The avalanche and hypothermia protective system includes a sensor housing to be worn by a user having a sensing device for detecting emergency situations, wherein the sensors are mounted in the sensor housing and are able to monitor bodily and environmental conditions affecting the user. The avalanche and hypothermia protective system is able to provide a supply of oxygen to a user upon detection of a severely impaired respiratory rate and/or the level or amount of oxygen in the surrounding atmosphere is determined to be below a predetermined level. The avalanche and hypothermia protective system also includes a vest and pants combination and a back pack to be worn by the user to aid in providing relief of sensed emergency conditions. Alternatively, the avalanche and hypothermia protective system may include a single piece body suit to be worn by the user. The avalanche and hypothermia protective system is able to provide a flow of heating thermal fluid through the vest and pants or one piece garment upon detection of a low body temperature and is able to transmit a distress signal upon detection of impact of a large amount of snow atop the user. Furthermore, the avalanche and hypothermia protective gear of the present invention is simple and easy to use and economical in cost to manufacture.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. Avalanche and hypothermia protective system for detecting an emergency situation affecting the user of the system and providing relief for the detected emergency situation, said system comprising:

a) a housing to be worn on the head of the user, said housing including at least one sensor therein for sensing a condition and generating a signal indicative of the sensed condition;

b) a backpack including a microprocessor therein connected to the at least one sensor for analyzing said signal generated by said at least one sensor and determining if an emergency situation exists; and c) means for relieving said emergency condition connected to said microprocessor for providing relief to the user upon determination by said microprocessor that an emergency condition exists.

2. The avalanche and hypothermia protective system as recited in claim 1, wherein said at least one sensor senses a skin temperature of the user and said system further comprises a vest including means for heating, whereby said means for relieving activates said means for heating upon determination by said microprocessor that an emergency condition exists.

3. The avalanche and hypothermia protective system as recited in claim 2, wherein said means for heating includes a plurality of tubes extending through an area of the vest and said means for relieving includes a chemical heat pack for storing a heating fluid, wherein said heating fluid is caused to flow through said plurality of tubes to thereby warm the user upon a determination that an emergency condition exists by said microprocessor.

4. The avalanche and hypothermia protective system as recited in claim 3, said system further comprises a pair of pants including means for heating, said means for heating said pants being connected to said means for heating said vest, whereby said means for relieving activates both said means for heating said pants and said means for heating said vest upon determination by said microprocessor that an emergency condition exists.

5. The avalanche and hypothermia protective system as recited in claim 4, wherein said means for heating said pair of pants includes a plurality of tubes extending through an area of the pair of pants connected to said plurality of tubes extending through said area of said vest, wherein said heating fluid is caused to flow through said plurality of tubes extending through said vest and said plurality of tubes extending through said pair of pants to thereby warm the user upon determination that an emergency condition exists by said microprocessor.

6. The avalanche and hypothermia protective system as recited in claim 5, said system further comprises a pair of socks including means for heating, said means for heating said socks being connected to said means for heating said pair of pants, whereby said means for relieving activates said means for heating said socks, said means for heating said pants and said means for heating said vest upon determination that an emergency condition exists by said microprocessor.

7. The avalanche and hypothermia protective system as recited in claim 6, wherein said means for heating said pair of socks includes a plurality of tubes extending through an area of the pair of sock connected to said plurality of tubes extending through said area of said pair of pants, wherein said heating fluid is caused to flow through said plurality of tubes extending through said vest, said plurality of tubes extending through said pair of pants and said plurality of tubes extending through said pair of socks to thereby warm the user upon determination that an emergency condition exists by said microprocessor.

8. The avalanche and hypothermia protective system as recited in claim 1, further comprising a one piece body suit including means for heating, whereby said means for relieving activates said means for heating upon determination by said microprocessor that an emergency condition exists.

9. The avalanche and hypothermia protective system as recited in claim 1, wherein said at least one sensor senses a respiration rate of the user and said means for relieving includes an oxygen supply for supplying oxygen to said user, whereby said oxygen supply means supplies oxygen to said user upon a determination by said microprocessor that an emergency condition exists.

10. The avalanche and hypothermia protective system as recited in claim 9, further comprising a connection tube secured to and extending through said housing for providing oxygen from said oxygen supply tank to a mouth and nose of the user.

11. The avalanche and hypothermia protective system as recited in claim 1, wherein said means for relieving includes a locator signal transmitter connected to transmit a distress signal upon determination by said microprocessor of an emergency situation.

12. The avalanche and hypothermia protective system as recited in claim 1, wherein said means for relieving includes an oxygen supply tank and said at least one sensor senses an oxygen level in the atmosphere surrounding the user, wherein said oxygen tank is controlled by said microprocessor to supply oxygen to the user upon a determination by said microprocessor that sensed oxygen level is below a predetermined amount.

13. The avalanche and hypothermia protective system as recited in claim 11, wherein said at least one sensor senses a noise level for the area in which the user is present.

14. The avalanche and hypothermia protective system as recited in claim 1, further comprising a supply of a liquid refreshment positioned within said backpack, a tube extending between said supply and a mouth of the user and a manually controlled dispenser for activating said supply to deliver said liquid refreshment through said tube to the mouth of the user upon demand.

15. The avalanche and hypothermia protective system as recited in claim 1, wherein said at least one sensor includes a plurality of sensors.

16. The avalanche and hypothermia protective system as recited in claim 15, wherein said plurality of sensors include any combination of a skin temperature sensor, a respiration rate sensor, a snow weight sensor, an oxygen pressure sensor, a water sensor and a noise sensor.

17. The avalanche and hypothermia protective system as recited in claim 16, wherein said means for relieving includes any combination of an oxygen supply, a chemical heat pack and a transmitter.

18. The avalanche and hypothermia protective system as recited in claim 17, further comprising a vest, pair of pants, and pair of socks, each including heating means connected to and controlled by said means for relieving for heating the body of the user upon a determination of an emergency situation by said microprocessor.

19. The avalanche and hypothermia protective system as recited in claim 17, further comprising a one piece body suit including heating means connected to and controlled by said means for relieving for heating the body of the user upon a determination of an emergency situation by said microprocessor.

20. The avalanche and hypothermia protective system as recited in claim 18, wherein said microprocessor includes means for comparing said generated signal to a reference value and means for controlling said means for relieving upon determining an emergency situation exists.

21. The avalanche and hypothermia protective system as recited in claim 19, wherein said microprocessor includes means for comparing said generated signal to a reference value and means for controlling said means for relieving upon determining an emergency situation exists.

* * * * *